United States Patent [19]
Batz

[11] Patent Number: 6,081,734
[45] Date of Patent: Jun. 27, 2000

[54] MONITORING SYSTEM FOR THE REGULAR INTAKE OF A MEDICAMENT

[75] Inventor: Hans-Georg Batz, Tutzing, Germany

[73] Assignee: Roche Diagnostics GmbH, Mannheim, Germany

[21] Appl. No.: 09/147,601

[22] PCT Filed: Aug. 1, 1997

[86] PCT No.: PCT/DE97/01653

§ 371 Date: Jan. 29, 1999

§ 102(e) Date: Jan. 29, 1999

[87] PCT Pub. No.: WO98/07364

PCT Pub. Date: Feb. 26, 1998

[30] Foreign Application Priority Data

Aug. 16, 1996 [DE] Germany .......................... 196 33 025

[51] Int. Cl.$^7$ ................................................ A61B 5/00
[52] U.S. Cl. .................................... 600/314; 600/317
[58] Field of Search ............................. 600/310, 314, 600/317, 322, 347, 365; 424/9.6, 9.61

[56] References Cited

U.S. PATENT DOCUMENTS

| | | |
|---|---|---|
| 4,867,557 | 9/1989 | Takatani et al. . |
| 5,028,787 | 7/1991 | Rosenthal et al. . |
| 5,036,861 | 8/1991 | Sembrowich et al. . |
| 5,057,695 | 10/1991 | Hirao et al. . |
| 5,187,672 | 2/1993 | Chance et al. . |
| 5,200,891 | 4/1993 | Kehr et al. . |
| 5,285,783 | 2/1994 | Secker . |
| 5,487,384 | 1/1996 | Lee . |
| 5,572,996 | 11/1996 | Doiron et al. ............................ 600/310 |
| 5,770,454 | 6/1998 | Essenpreis et al. . |
| 5,804,371 | 9/1998 | Höss et al. . |

FOREIGN PATENT DOCUMENTS

| | | |
|---|---|---|
| 0 689 848 | 1/1996 | European Pat. Off. . |
| 2 257 356 | 3/1974 | Germany . |
| 39 40 260 | 9/1990 | Germany . |
| 39 35 257 | 4/1991 | Germany . |
| 2 309 166 | 7/1997 | United Kingdom . |

OTHER PUBLICATIONS

International Publication No. WO 92/17108, published Oct. 15, 1992.
International Publication No. WO 94/00602, published Jan. 6, 1994.
International Publication No. WO 96/03650, publishied Feb. 8, 1996.
International Publication No. WO 96/03410, published Feb. 8, 1996.
International Publication No. WO 92/15013, published Sep. 3, 1992.
Article by P. W. Nicholson from Med. & Biol. Eng. Comput., 1994, 29, 609–608.

*Primary Examiner*—Eric F. Winakur
*Attorney, Agent, or Firm*—Arent Fox Kintner Plotkin & Kahn, PLLC

[57] ABSTRACT

A control system for monitoring the regular intake of a medicament by a patient. The system comprises system components mutually tuned to each other and comprising a medicine dosage form (1) for the medication and a detection apparatus (2) for non-invasive detection, within the body of the patient, of a detection substance contained in the medicine dosage form (3). The detection apparatus (2) is adapted for reagent-free direct measurement of a physically measurable parameter correlated with the presence of the detection substance in the body of the patient.

42 Claims, 2 Drawing Sheets

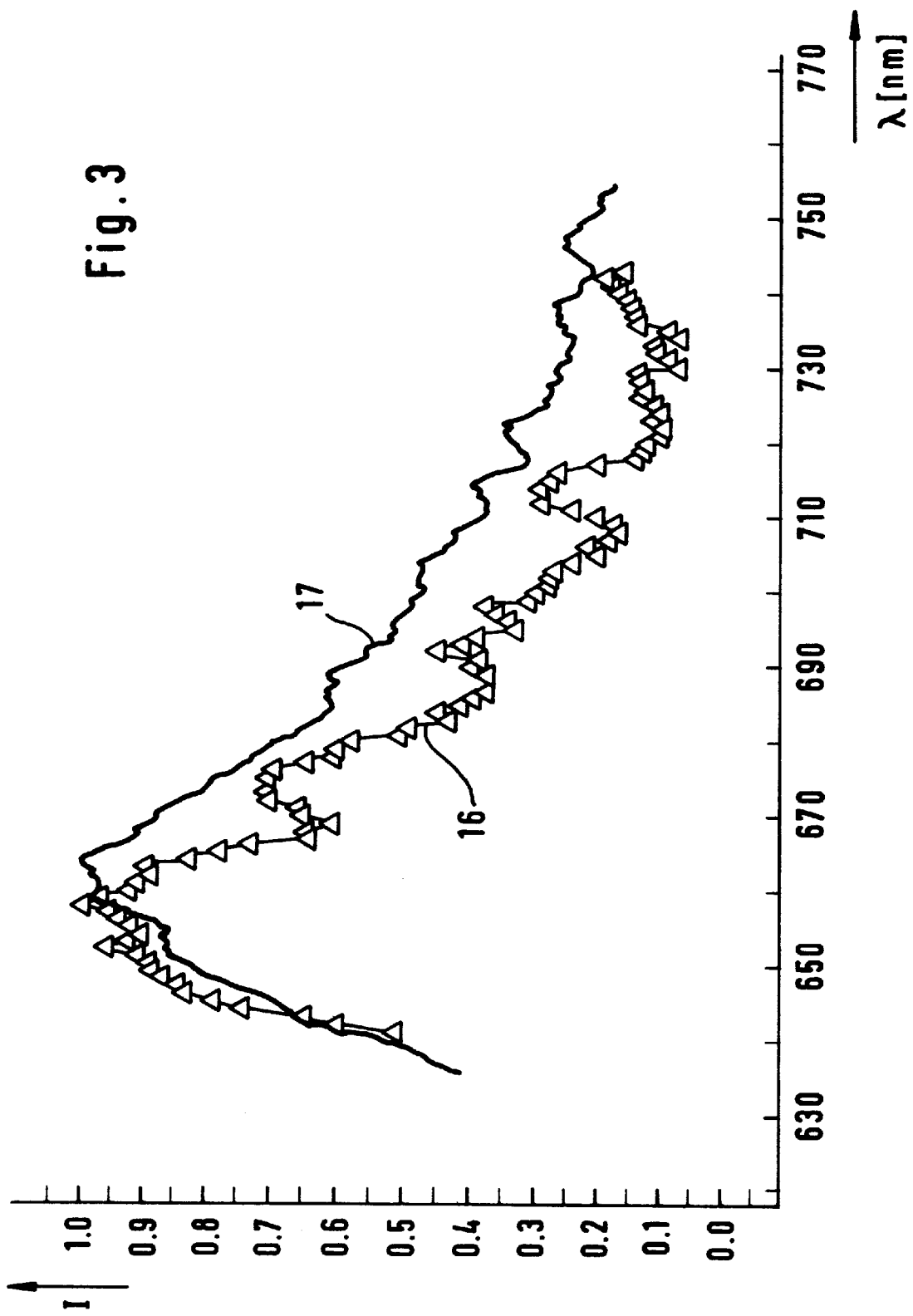

MONITORING SYSTEM FOR THE REGULAR INTAKE OF A MEDICAMENT

The invention concerns a system for monitoring the regular intake of a medicament by a patient as well as a medicine dosage form for such a monitoring system.

The regular intake of a medicament is often of great importance for its effectiveness. For example with antibiotics, a premature termination leads to reoccurrence of the disease or to the generation of resistance. Nevertheless, medicine is often not taken regularly according to prescription or intake is interrupted at a premature stage. For certain therapies with which the regular intake of the medication is of great importance (e.g. TBC, HIV and other serious infectious diseases) in-patient treatment in the hospital is therefore required in order to guarantee the individual monitoring of the regular administering of the medicine. Such an in-patient treatment for the sole reason of monitoring the intake of the medication can be disadvantageous to the recuperation processes and is very expensive.

There is therefore an urgent need for a reliable monitoring of the regular intake of medication at reasonable expense. There is no current solution to this problem. For some therapies involving medication, analytical investigations of the concentration of the medication in the blood (so-called "drug tests") are carried out to adjust the optimum effective concentration of the drug. Such analytical procedures are, however, only available for a small number of medicaments and require the removal of blood for each investigation as well as performing a relatively difficult analysis procedure. Drug tests do not allow self-monitoring of the intake of a medication by the patient and also do not allow the physician to monitor the regular intake of the medication without the cooperation of the patient.

In order to solve this problem, the invention proposes a monitoring system which includes, as mutually adapted system components, a dosage form of the medicament and a detection apparatus for non-invasive detection of a substance contained in the dosage form (subsequently referred to as "detection substance") in the body of the patient. The detection apparatus is adapted for reagent-free direct measurement of a measuring quantity correlating with the presence of the detection substance in the body of the patient.

In the most general form of the invention, the detection substance can be formed by the medication itself i.e. the therapeutically active agent. This is, however, limited to active agents which can be detected in a non-invasive manner. Nearly all chemotherapy medicaments have characteristic IR bands which can be utilized for such detection. Examples of medication which facilitate non-invasive detection are: antibiotics such as tetracycline, nitrofurone and nalidixic acid, the tuberculosis medicaments rifampicin and isonicotinic acid hydrazide, the malaria medicament Chloroquine sulphate and also anticoagulant agents such as maramar and heart/circulation medication such as nitroglycerin and digoxin.

In other cases the typical IR-bands are overlapped by the bands of substances naturally present in the body. In such cases or in the event that the concentration of the effective agent is too small, the non-invasive detectable substance contained in the dosage form is, according to a preferred embodiment of the invention, a non-toxic marking substance differing from the medication (active agent). The marking substance is selected such that it does not encroach upon the pharmaceutical effectiveness of the medicament's active agent and has no additional negative side effects in the body of the patient (preferentially it is completely inert within the body) while nevertheless allowing easy detection of its presence in the body of the patient. This embodiment allows to optimize the marking substance with respect to ease of detection thereof. In accordance with a preferred embodiment of the invention, damaging toxic effects on the body can, if necessary, be avoided by capsulation or bonding within a macromolecular protective molecular structure, in particular a protective molecule selected from the group of dendrimeres or fullvalenes.

The invention is further described below in connection with use of a dedicated marking substance which is separate from the drug. This, however, does not limit the generality for cases where the active agent itself has properties making it suitable as detection substance.

Widely differing physically measurable quantities can be used as the measurement quantity. Examples are the intensity, the frequency or the phase of electromagnetic radiation (in particular light in the IR or visible range), the intensity, frequency or phase of an acoustical signal or the intensity or polarity of a magnetic field. The measurement quantity has to be such that it is influenced by the presence of the marking substance in the body of the patient in a measurable fashion so that a change in the concentration of the marking substance associated with the intake of the medicament can be detected through measurement thereof using the detection apparatus. Such a measurement quantity is subsequently designated, in accordance with customary English language usage ("quantifiable parameter"), as "parameter".

In accordance with the invention, it is normally not necessary to quantitatively determine the concentration of the marking substance in the body of the patient. Rather preferentially the detection apparatus comprises means for determining the time dependent change of the parameter. The required electronic means for differentiation or for determination of difference ratios from a measurement signal are known in the art. Preferably an increase or decrease of the parameter measurement signal is utilized as an indication for the intake of the medicament, i.e. an output signal corresponding to the "detection" of the marking substance is produced when the parameter measurement signal increases or decreases at a predetermined minimal threshold rate of change.

The invention is suitable for a variety of pharmaceutical dosage forms. It is particularly important for oral applications (tablets, capsules, or the like) but is-also usable for other dosage forms such as suppositories or injections whenever monitoring of the regular application of the medicament is required. Clearly, the marking substance must be brought into a pharmaceutical form suitable for the corresponding dosage form.

As mentioned, the invention can be embodied with differing operation principles, i.e. based on completely differing interactions between the marking substance and the detection apparatus. A few preferred examples are described below.

In a first embodiment, the marking substance has dye properties, preferentially in the IR-region of the optical spectrum. An appropriate detection apparatus irradiates light of an appropriate wavelength through the skin into the body of the patient and measures the light coming out of the body following interaction with the components contained therein (and thereby also with the marking substance). The system components are advantageously adjusted and adapted to each other in such a manner that as high an intensity of the irradiated light as possible lies in a spectral region in which the marking substance has an absorption maximum. These wavelengths are preferentially chosen such that they lie outside of the absorption maxima of optically absorbing substances contained in high concentration in the body of the patient (in particular within the skin) and, in particular, outside of the absorption bands of water and hemoglobin.

Once the marking substance and the associated detection wavelength are chosen, conventional processes for detection of components in the body, in particular within the human skin, can be utilized. Such methods are known in the art in particular for non-invasive analysis of analytes important for oxygenation processes in human beings (hemoglobin, desoxihemoglobin, and cytochrome a and a3). Towards this end, reference is hereby made e.g. to U.S. Pat. No. 5,028,787 (Rosenthal et al.) with a plurality of references to previous publications and to U.S. Pat. No. 5,285,783 (Secker).

In such IR detection procedures, the light is normally irradiated at a plurality of wavelengths and the spectral dependence of the measured parameter of the light is utilized to detect the target substance. The present invention also preferentially operates with a plurality of wavelengths in order to spectroscopically detect the marking substance.

A particularly suitable operation principle is based on the use of a fluorescent dye as a marking substance, wherein the detection apparatus is adapted for in vivo detection of the fluorescence. Towards this end, light is irradiated into the body of the patient whose wavelength corresponds to the absorption wavelength of the fluorescent dye. Lasers are particularly well suited as light sources therefor. The resulting fluorescence radiation is detected in a wavelength selective manner. Preferably fluorescence dyes which emit in the longest wavelength region of visible light and in the near infrared are used. Wavelengths between approximately 600 nm and approximately 800 nm are particularly preferred. Despite the low intensity of the emitted fluorescent light, this interaction mechanism has turned out to be particularly well suited for the purposes of the invention, since the overlap of the usable signal with interfering signals is relatively low so that a good signal to noise ratio compared to other processes results.

In several known methods which are likewise suitable in the present invention for non-invasive detection of analytes in the human body, light is irradiated at differing radiation locations through the skin into the body and/or light coming out of the skin is detected at differing detection locations so that the light travels from the corresponding irradiation location to the detection location along differing light paths. The measurement signals measured for the differing light paths are further processed to provide the desired analytic information. This method strives to direct the analysis in a defined fashion to certain layers within the skin tissue. A method of this kind is e.g. described in U.S. Pat. No. 4,867,557 (Takatani) and in U.S. Pat. No. 5,057,695 (Hirao).

In a further known method of non-invasive analysis, so-called "frequency domain spectroscopic measurements" are carried out. Here the irradiated light is modulated with a radio frequency and the frequency shift or the degree of modulation of the detected light relative to the irradiated light is utilized as the parameter correlated with the presence of the analyte. In this respect reference is made to U.S. Pat. No. 5,187,672 to Chance, the publications cited therein as well as to WO 95/32416. This procedure can also be advantageously utilized within the framework of the present invention.

Suitable marking substances can for example be molecules developed as marker molecules for diagnostic applications. Examples are:

Fluorescing marking substances, in particular fluorescein and fluorescence metallic complex compounds such as those disclosed in WO 96/03410.

Detection substances developed for immunological detection methods such as DNA-diagnostics as described in WO 96/03650.

Absorption or fluorescent dyes, e.g. in accordance with EP-B-0567622.

In certain cases ferromagnetic microparticles whose magnetic interaction can be detected through the skin can also be used as marking substances.

Furthermore electromagnetic radiation having a wavelength outside the visible spectrum, preferentially in the range of radio waves and microwaves, can also be used as a probe to detect the presence of a marking substance within the body of the patient. In this case, in particular substances having diode properties can be utilized as marking substances. Details are described in WO 92/15013. Here the marking substance thereby has a p-n-transition causing diode behavior, i.e. in an electric field the substance conducts in one field direction and has a high resistance in the other field direction. Such semiconductor diodes can be produced in a micro-miniaturized form so that they are, in principle, suitable as marking substances within a medicament. Detection is effected through the interaction with a high frequency signal, preferentially in the MHz-range as described in the cited publication WO 92/15013.

The invention is further described below with reference to the figures in which an embodiment of the invention is shown.

FIG. 2 shows a block diagram of a detection apparatus and an eternal inquiry unit and FIG. 3 shows a graphical representation of a spectrum for one embodiment of the invention.

The control system consists essentially of a medicine dosage form 1 (here a tablet) containing a marking substance symbolically designated by a star, and a detection apparatus 2 which, in the preferred embodiment shown, is embodied as a wristwatch worn by the patient 3. Such a detection apparatus configured in the form of a device normally worn on the body performs its monitoring function in an inconspicuous manner and does not cause discomfort to the patient. In general, the monitoring apparatus should be sufficiently small and light to be easily carried.

Figure 1:
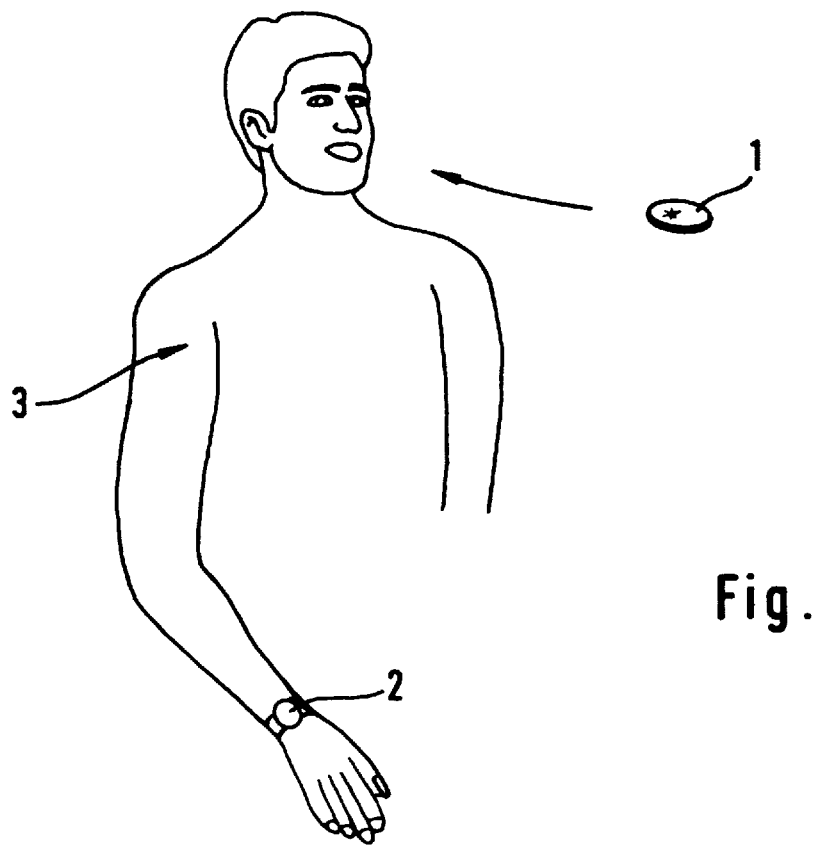
FIG. 1 shows a schematic view of the system components.
Figure 2:
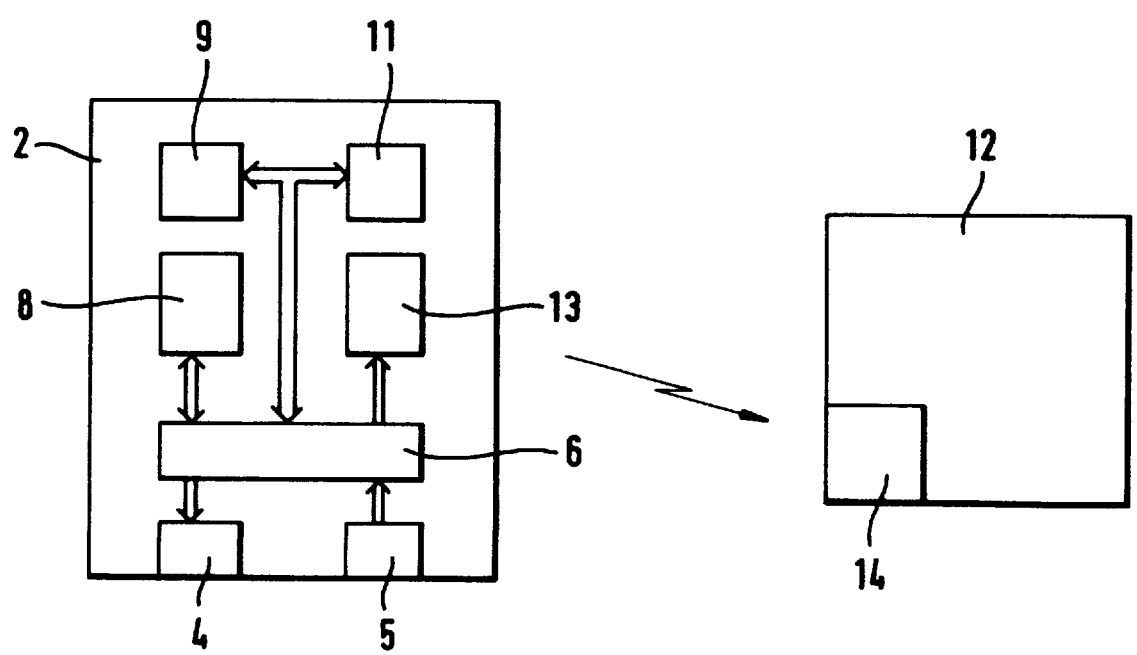

The important components of the detection apparatus 2 are shown in FIG. 2 in the form of a block diagram. It contains irradiation and detection means 4 and 5 e.g. in the form of light diodes and semiconductor light detectors. The signals of the detection means are processed by a measurement and analysis circuit 6 (e.g. using one of the methods described in the cited publications) into data concerning the presence of the marking substances in the body of the patient 3. These data are stored in a memory 8 of the apparatus 2. A time measurement device 9 is provided in order to query the measurement time and to also store same in the memory 8.

The detection apparatus can be of relatively simple design compared to the known methods for non-invasive analysis of substances in the human body mentioned above, since there is no need to determine absolute concentrations. It is sufficient to detect the increase in concentration of the marking substance associated with the intake of the medicament. This can e.g. be effected using a threshold value or (preferentially) through the determination of the time change of the parameter (i.e. taking the first derivative of the measurement signal). No sophisticated calibration procedures are necessary.

The data stored in the memory 8 can be further processed in a conventional manner by the micro processor controlled measurement and analysis unit. In particular, same can contain a program by means of which monitor measurements can be initiated at certain predetermined times (e.g. once daily) in order to check whether the patient has taken the medicament which then can be detected. The program can also, in the event of a negative result for the monitoring, produce a warning signal by driving an acoustical signal transmitter 11 to advise the patient concerning the intake of the medication. This can be modified in various ways. One can e.g. remind the patient to take the medicament, without previous monitoring, using a tone and check intake thereof within a subsequent certain defined period of time through detection of the marking substance with the assistance of the detection apparatus 2.

In order to simplify a long-term monitoring of the regular intake by the patient himself and/or by the responsible physician, the data concerning the detection of the marking substance and the measuring times can be transferred from the detection apparatus 2 to an external data reception unit 12. This external data reception unit can be located at the patient himself or at the physician. Clearly, the patient and the physician can have the same or differing data reception units. In general, the detection apparatus 2 and the data reception unit 12 should be configured in such a fashion that the patient can neither erase nor manipulate data concerning the detection of the marking substance.

Transfer of the data from the detection apparatus 2 to the external data reception unit 12 is performed in a wireless manner in the preferred embodiment shown, wherein the detection apparatus 2 has a transmitter 13 and the data reception unit 12 has a receiver 14. Transmission is effected e.g. using infrared radiation or via FM radio signals. Alternatively, a data port for cable transmission to the detection apparatus 2 can be provided for to which the external data reception unit 12 is connected from time to time using a cable.

Investigation of the in vivo detectability of a suitable marking substance was carried out in an animal experiment. Mice were fed with a food dye approved by the FDA, designated Brilliant Blue FCF. The fluorescence of this fluorescent dye was measured in vivo at the ears of the mice. Excitation was effected using a helium neon laser having a power of 1.5 mW and a wavelength of 632.8 nm. Fluorescent radiation was detected using fiber optics at the ears of the mice and focussed onto the emission monochromator of a fluorescent spectrometer. The resulting spectrum, normalized to the maximum value, is shown in FIG. 3, wherein the intensity I (relative to the maximum value in each case) is plotted versus wavelength in nm. The measured curve 16 shows the result of the in vivo measurement at the ear (triangular measuring points). The measurement curve 17 compares the results, likewise normalized to the maximum value, for an in vitro measurement of the spectrum of the dye with the same spectrometer. The in vivo measurement agrees very well with the in vitro measurement. One can thereby conclude that changes in the concentration of a physiologically safe dye can be reliably detected in vivo using relatively simple means and at a suitable wavelength (in particular near the maximum of the emission spectrum).

What is claimed is:

1. System for monitoring the regular intake of a medicament by a patient, characterized in that, it includes mutually adapted system components comprising a medicine dosage form containing the medicament and a detection apparatus for non-invasive detection of a substance contained in the dosage form within the body of a patient, wherein the non-invasively detectable substance contained in the dosage form is a non-toxic marking substance which differs from the medicament and the detection apparatus is adapted for reagent-free direct measurement of a physically measurable parameter correlated with the presence of the substance in the body of the patient and comprises determination means for determination of the time dependent change of the parameter to detect intake of the medicament.

2. Monitoring system according to claim 1, characterized in that the marking substance measurably influences electromagnetic radiation irradiated into the body and the detection apparatus comprises irradiation means for the irradiation of electromagnetic radiation into the body of the patient as well as detection means for measurement of a measuring quantity of the exiting radiation following interaction between the electromagnetic radiation and the marking substance, as a parameter correlated to the presence thereof in the body.

3. Monitoring system according to claim 2, characterized in that the electromagnetic radiation is light.

4. Monitoring system according to claim 3, characterized in that the irradiation means are configured for irradiation of a plurality of wavelengths of the electromagnetic radiation and the spectral dependence of the parameter is utilized for detection of the marking substance.

5. Monitoring system according to claim 3, characterized in that the light is in the visible or infrared range of the optical spectrum.

6. Monitoring system according to claim 3, characterized in that the detection apparatus comprises irradiation means for irradiation of the electromagnetic radiation at a plurality of differing irradiation locations and/or detection means for detection of the electromagnetic radiation at a plurality of differing detection locations and the marking substance is detected on the basis of the dependence of the detected parameter on the measuring distance between a respective irradiation location and a respective detection location.

7. Monitoring system according to claim 1, characterized in that the marking substance contains a fluorescent dye and the detection apparatus is adapted for in vivo detection of the fluorescence as the parameter is correlated to the presence of the marking substance in the body.

8. Monitoring system according to claim 1, characterized in that the detection apparatus comprises a sensor unit which can be carried on the body.

9. Monitoring system according to claim 1, characterized in that the detection apparatus is configured in the form of a device conventionally worn on the body.

10. Monitoring system according to claim 9, wherein the device is a wrist watch.

11. Monitoring system according to claim 1, characterized in that the detection apparatus comprises a time measuring device and a memory for the storage of data concerning the detection of the marking substance.

12. Monitoring system according to claim 11, characterized in that the detection apparatus produces a warning signal if no marking substance is detectable within the body of the patient within a predetermined period of time.

13. Monitoring system according claim 1 characterized in that the detection apparatus comprises a port for the transfer of data to an external inquiry unit.

14. Monitoring system according to claim 1, characterized in that the detection apparatus comprises a transmitter for the wireless transmission of the data to an external inquiry unit.

15. Medicine dosage form for a monitoring system according to claim 1, characterized in that the dosage form includes, in addition to an active agent, a non-toxic marking substance whose presence in the body of the patient can be measured in a non-invasive fashion using the detection apparatus.

16. Medicine dosage form according to claim 15, characterized in that the marking substance contains a fluorescent dye.

17. Medicine dosage form according to claim 15, characterized in that the marking substance is rendered non-toxic by capsulation or by incorporation within a macromolecular protective molecular structure.

18. Medicine dosage form according to claim 17, characterized in that the macromolecular protective molecular structure belongs to the group comprising dendrimeres and fullvalenes.

19. System for monitoring the regular intake of a medicament by a patient, characterized in that, it includes mutually adapted system components comprising a medicine dosage form containing the medicament and a detection apparatus for non-invasive detection of a substance contained in the dosage form within the body of a patient, wherein the detection apparatus is adapted for reagent-free direct measurement of a physically measurable parameter correlated with the presence of the substance in the body of the patient and comprises determination means for determination of the time dependent change of the parameter to detect intake of the medicament, the medicament measurably influences electromagnetic radiation irradiated into the body and the detection apparatus comprises irradiation means for the irradiation of light into the body of the patient as well as detection means for measurement of a measuring quantity of the exiting light following interaction between the electromagnetic radiation and the medicament, as a parameter correlated to the presence thereof in the body and the irradiation means are configured for irradiation of a plurality of wavelengths of the electromagnetic radiation and the spectral dependence of the parameter is utilized for detection of the marking substance.

20. Monitoring system according to claim 19, characterized in that the light is in the visible or infrared range of the optical spectrum.

21. Monitoring system according to claim 19, characterized in that the marking substance contains a fluorescent dye and the detection apparatus is adapted for in vivo detection of the fluorescence as the parameter is correlated to the presence of the marking substance in the body.

22. Monitoring system according to claim 19, characterized in that the detection apparatus comprises a sensor unit which can be carried on the body.

23. Monitoring system according to claim 19, characterized in that the detection apparatus is configured in the form of a device conventionally worn on the body.

24. Monitoring system according to claim 19, characterized in that the detection apparatus comprises a time measuring device and a memory for the storage of data concerning the detection of the marking substance.

25. Monitoring system according to claim 24, characterized in that the detection apparatus produces a warning signal if no marking substance is detectable within the body of the patient within a predetermined period of time.

26. Monitoring system according to claim 19, characterized in that the detection apparatus comprises a port for the transfer of data to an external inquiry unit.

27. Monitoring system according to claim 19, characterized in that the detection apparatus comprises a transmitter for the wireless transmission of the data to an external inquiry unit.

28. Medicine dosage form for a monitoring system according to claim 19, characterized in that the dosage form includes, in addition to an active agent, a non-toxic marking substance whose presence in the body of the patient can be measured in a non-invasive fashion using the detection apparatus.

29. System for monitoring the regular intake of a medicament by a patient, characterized in that, it includes mutually adapted system components comprising a medicine dosage form containing the medicament and a detection apparatus for non-invasive detection of a substance contained in the dosage form within the body of a patient, wherein the detection apparatus is adapted for reagent-free direct measurement of a physically measurable parameter correlated with the presence of the substance in the body of the patient and comprises determination means for determination of the time dependent change of the parameter to detect intake of the medicament,
the medicament measurably influences electromagnetic radiation irradiated into the body and the detection apparatus comprises irradiation means for the irradiation of light into the body of the patient as well as detection means for measurement of a measuring quantity of the exiting light following interaction between the electromagnetic radiation and the medicament, as a parameter correlated to the presence thereof in the body and the detection apparatus comprises irradiation means for irradiation of the light at a plurality of differing irradiation locations and/or detection means for detection of the light at a plurality of differing detection locations and the marking substance is detected on the basis of the dependence of the detected parameter on the measuring distance between an irradiation location and a detection location.

30. Monitoring system according to claim 29, characterized in that the light is in the visible or infrared range of the optical spectrum.

31. Monitoring system according to claim 29, characterized in that the marking substance contains a fluorescent dye and the detection apparatus is adapted for in vivo detection of the fluorescence as the parameter is correlated to the presence of the marking substance in the body.

32. Monitoring system according to claim 29, characterized in that the detection apparatus comprises a sensor unit which can be carried on the body.

33. Monitoring system according to claim 29, characterized in that the detection apparatus is configured in the form of a device conventionally worn on the body.

34. Monitoring system according to claim 29, characterized in that the detection apparatus comprises a time measuring device and a memory for the storage of data concerning the detection of the marking substance.

35. Monitoring system according to claim 34, characterized in that the detection apparatus produces a warning signal if no marking substance is detectable within the body of the patient within a predetermined period of time.

36. Monitoring system according to claim 29, characterized in that the detection apparatus comprises a port for the transfer of data to an external inquiry unit.

37. Monitoring system according to claim 29, characterized in that the detection apparatus comprises a transmitter for the wireless transmission of the data to an external inquiry unit.

38. Medicine dosage form for a monitoring system according to claim 29, characterized in that the dosage form includes, in addition to an active agent, a non-toxic marking substance whose presence in the body of the patient can be measured in a non-invasive fashion using the detection apparatus.

39. System for monitoring the regular intake of a medicated by a patient, characterized in that, it includes mutually adapted system components comprising a medicine dosage form containing the medicament and a detection apparatus for non-invasive detection of a substance contained in the dosage form within the body of a patient, wherein the detection apparatus is adapted for reagent-free direct measurement of a physically measurable parameter correlated with the presence of the substance in the body of the patient and comprises determination means for determination of the time dependent change of the parameter to detect intake of the medicament and the detection apparatus comprises a sensor unit which can be carried on the body.

40. System for monitoring the regular intake of a medicament by a patient, characterized in that, it includes mutually adapted system components comprising a medicine dosage form containing the medicament and a detection apparatus for non-invasive detection of a substance contained in the dosage form within the body of a patient, wherein the detection apparatus is adapted for reagent-free direct measurement of a physically measurable parameter correlated with the presence of the substance in the body of the patient and comprises determination means for determination of the time dependent change of the parameter to detect intake of the medicament and the device is a wrist watch.

41. System for monitoring the regular intake of a medicament by a patient, characterized in that, it includes mutually adapted system components comprising a medicine dosage form containing the medicament and a detection apparatus for non-invasive detection of a substance contained in the dosage form within the body of a patient, wherein the detection apparatus is adapted for reagent-free direct measurement of a physically measurable parameter correlated with the presence of the substance in the body of the patient and comprises determination means for determination of the time dependent change of the parameter to detect intake of the medicament and the detection apparatus comprises a time measuring device and a memory for the storage of data concerning the detection of the marking substance.

42. System for monitoring the regular intake of a medicament by a patient, characterized in that, it includes mutually adapted system components comprising a medicine dosage norm containing the medicament and a detection apparatus for non-invasive detection of a substance contained in the dosage form within the body of a patient, wherein the detection apparatus is adapted for reagent free direct measurement of a physically measurable parameter correlated with the presence of the substance in the body of the patient and comprises determination means for determination of the time dependent change of the parameter to detect intake of the medicament and the detection apparatus produces a warning signal if no marking substance is detectable within the body of the patient within a predetermined period of time.

* * * * *